US010084230B2

(12) United States Patent
Hong et al.

(10) Patent No.: US 10,084,230 B2
(45) Date of Patent: Sep. 25, 2018

(54) WEARABLE BODY SENSOR AND SYSTEM INCLUDING THE SAME

(71) Applicant: Samsung Electronics Co., Ltd., Suwon-si (KR)

(72) Inventors: Young Jun Hong, Seoul (KR); Won Bin Hong, Seoul (KR); Byung Hoon Ko, Hwaseong-si (KR); Byung Chul Kim, Hwaseong-si (KR); Young Soo Kim, Seoul (KR); Yoon Geon Kim, Busan (KR); Young Ju Lee, Seoul (KR); Jae Chun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 299 days.

(21) Appl. No.: 14/508,602

(22) Filed: Oct. 7, 2014

(65) Prior Publication Data

US 2015/0102939 A1   Apr. 16, 2015

(30) Foreign Application Priority Data

Oct. 14, 2013 (KR) .................. 10-2013-0121675

(51) Int. Cl.
*H01Q 1/00* (2006.01)
*H01Q 1/27* (2006.01)
(Continued)

(52) U.S. Cl.
CPC ........... *H01Q 1/273* (2013.01); *A61B 5/0015* (2013.01); *A61B 5/01* (2013.01); *A61B 5/02* (2013.01);
(Continued)

(58) Field of Classification Search
CPC ........ A61B 1/00016; A61B 2560/0271; A61B 2560/0412; A61B 2560/0468;
(Continued)

(56) References Cited

U.S. PATENT DOCUMENTS 6,289,238 B1 * 9/2001 Besson .............. A61B 5/14552
128/903
6,577,893 B1   6/2003 Besson et al.
(Continued)

FOREIGN PATENT DOCUMENTS

CN   103117456 A   5/2013
JP   11-220324 A   8/1999
(Continued)

OTHER PUBLICATIONS

Silveira, M. Hernandez, et al. "Key Considerations and Experience Using the Ultra Low Power Sensium Platform in Body Sensor Networks." Sixth International Workshop on Wearable and Implantable Body Sensor Networks, (IEEE 2009) workshop held on Jun. 3-5, 2009, pp. 262-266.
(Continued)

*Primary Examiner* — Muhammad N Edun
*Assistant Examiner* — Jerold Murphy
(74) *Attorney, Agent, or Firm* — NSIP Law

(57) ABSTRACT

A body sensor, a system including the body sensor and a method of transmitting a biosignal are provided. A wearable body sensor includes a conductive electrode configured to conduct a biosignal from a body, a main board comprising a radio frequency (RF) communication circuit to generate an RF signal based on the biosignal, and an antenna disposed on the RF communication circuit to radiate the RF signal.

25 Claims, 19 Drawing Sheets

(51) Int. Cl.
| | |
|---|---|
| *A61B 5/01* | (2006.01) |
| *A61B 5/02* | (2006.01) |
| *A61B 5/024* | (2006.01) |
| *A61B 5/0402* | (2006.01) |
| *A61B 5/0488* | (2006.01) |
| *A61B 5/053* | (2006.01) |
| *A61B 5/00* | (2006.01) |
| *G08C 17/00* | (2006.01) |
| *H01Q 1/48* | (2006.01) |
| *H04B 13/00* | (2006.01) |

(52) U.S. Cl.
CPC ........ *A61B 5/02438* (2013.01); *A61B 5/0402* (2013.01); *A61B 5/0488* (2013.01); *A61B 5/053* (2013.01); *A61B 5/683* (2013.01); *G08C 17/00* (2013.01); *H01Q 1/48* (2013.01); *H04B 13/005* (2013.01); *A61B 5/0006* (2013.01); *A61B 5/0008* (2013.01); *A61B 2562/0271* (2013.01); *A61B 2562/166* (2013.01)

(58) Field of Classification Search
CPC ..... A61B 2562/182; A61B 5/00; A61B 5/681; H01Q 1/243; H01Q 1/521; H01Q 21/29; Y10S 128/903
See application file for complete search history.

(56) References Cited

U.S. PATENT DOCUMENTS

| | | | | |
|---|---|---|---|---|
| 6,762,728 | B2* | 7/2004 | Koyama | G04G 21/04 |
| | | | | 343/700 MS |
| 2005/0194012 | A1* | 9/2005 | Ito | A61B 1/041 |
| | | | | 128/899 |
| 2006/0155183 | A1 | 7/2006 | Kroecker et al. | |
| 2007/0285225 | A1 | 12/2007 | Koyama et al. | |
| 2010/0030088 | A1 | 2/2010 | Carney et al. | |
| 2010/0198044 | A1 | 8/2010 | Gehman et al. | |
| 2011/0043424 | A1* | 2/2011 | Lee | H01Q 1/246 |
| | | | | 343/816 |
| 2011/0128192 | A1* | 6/2011 | Lee | H01Q 1/243 |
| | | | | 343/702 |
| 2011/0166614 | A1 | 7/2011 | Abrahamson et al. | |
| 2011/0175783 | A1 | 7/2011 | Kim | |
| 2011/0193754 | A1* | 8/2011 | Schlub | H01Q 1/243 |
| | | | | 343/702 |
| 2012/0176279 | A1* | 7/2012 | Merz | H01Q 1/243 |
| | | | | 343/702 |
| 2012/0190952 | A1 | 7/2012 | Stafford | |
| 2013/0060115 | A1 | 3/2013 | Gehman et al. | |
| 2013/0116533 | A1 | 5/2013 | Lian et al. | |
| 2013/0176181 | A1* | 7/2013 | Mo | H01Q 1/243 |
| | | | | 343/702 |
| 2014/0043197 | A1* | 2/2014 | Lee | H01Q 19/10 |
| | | | | 343/833 |

FOREIGN PATENT DOCUMENTS

| | | |
|---|---|---|
| JP | 2007-525269 A | 9/2007 |
| JP | 4843611 B2 | 10/2011 |
| JP | 2013-512067 A | 4/2013 |
| KR | 10-2006-0017136 A | 2/2006 |
| KR | 10-2009-0092548 A | 9/2009 |
| KR | 10-2009-0130521 A | 12/2009 |
| KR | 10-2010-0119528 A | 11/2010 |
| KR | 10-2010-0120661 A | 11/2010 |
| KR | 10-2012-0065540 A | 6/2012 |
| KR | 10-2012-0072017 A | 7/2012 |

OTHER PUBLICATIONS

"Datasheet", Amotech Co., Ltd., Aug. 27, 2009.
Wong, A. C. W., et al. "Sensium: An Ultra-Low-Power Wireless Body Sensor Network Platform: Design & Application Challenges." 31st Annual International Conference of the IEEE Engineering in Medicine and Biology Society, conference held on Sep. 2-6, 2009, pp. 6576-6579.
Kim, S.H., "Application Report", Amotech/Antenna Gr., Jun. 9, 2011.
Hertleer, Carla, et al. "Off-body communication for protective clothing." Wearable and Implantable Body Sensor Networks, 2009. BSN 2009. Sixth International Workshop on. IEEE, 2009.
Extended European Search Report dated Mar. 6, 2015 in counterpart European Application No. EP 14170246.4.
Japanese Office Action dated Feb. 20, 2018 in corresponding Japanese Patent Application No. 2014-209217 (4 pages in English and 7 pages in Japanese).

* cited by examiner

FIG. 15
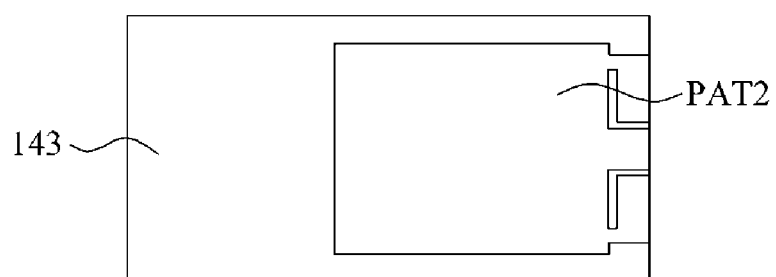
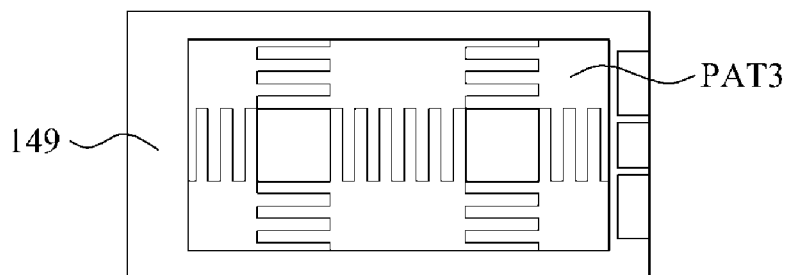

WEARABLE BODY SENSOR AND SYSTEM INCLUDING THE SAME

CROSS-REFERENCE TO RELATED APPLICATION

This application claims the benefit under 35 USC 119(a) of Korean Patent Application No. 10-2013-0121675 filed on Oct. 14, 2013, in the Korean Intellectual Property Office, the entire disclosure of which is incorporated herein by reference for all purposes.

BACKGROUND

1. Field

The following description relates to a wearable body sensor, a system that includes a wearable body sensor, and a method of transmitting a biosignal.

2. Description of Related Art

As the elderly population continues to increase, the number of patients suffering from heart disease, diabetes, and other related diseases is proportionally increasing. Accordingly, medical cost expenditure is increasing for the society. In the field of medicine, a device used to collect medical information of a patient has been evolving into an on-body form or an in-body form. These devices are sometimes referred to as body sensors, sensing devices, monitoring devices and the like. An on-body form device refers to a device that is worn on the body. An in-body form device refers to a device that is implanted into the body.

The device that may be worn on the body or implanted into the body may provide constant monitoring of a status of the patient, may measure a biosignal, may transmit data wirelessly, and may receive data wirelessly from an external source.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a wearable body sensor including a conductive electrode configured to conduct a biosignal from a body, a main board comprising a radio frequency (RF) communication circuit to generate an RF signal based on the biosignal, and an antenna disposed on the RF communication circuit to radiate the RF signal.

The body sensor may further include a ground layer disposed between the main board and the conductive electrode to reflect the RF signal radiated from the antenna to the body.

The body sensor may further include at least one electrical element configured to electrically connect the main board and the ground layer.

The body sensor may further include at least one electrical element configured to electrically connect the antenna and the ground layer.

The at least one electrical element may be provided in a form of a through-hole via.

The body sensor may further include an electrode interface configured to transmit the biosignal to the main board.

The body sensor may further include at least one electrical element configured to electrically connect the electrode interface and the main board.

The at least one electrical element may be provided in a form of a through-hole via.

The main board may be configured in a form of at least one segmented structure.

The antenna includes an antenna pattern configured to radiate the RF signal and an antenna layer disposed at an upper end of the RF communication circuit to be in a vertical feeding structure.

The antenna further includes an antenna carrier configured to support the antenna layer.

The antenna pattern may be configured to radiate the RF signal in a horizontal direction.

The antenna may further include an air bridge configured to electrically connect each ground pattern of the antenna pattern.

The antenna layer may further include a ground plane connected to the antenna pattern.

The ground plane may include at least one artificial magnetic conductor unit cell.

An antenna feeder of the antenna pattern may be connected to the main board through a coaxial jack, a C clip, or a pogo pin.

The body sensor may be configured to measure at least one of electrocardiogram, electromyogram, body temperature, pulse rate, electric conduction, vital signs and blood pressure of the body wearing the body sensor.

In another general aspect, a system includes a body sensor wearable on a body, and a host device configured to control the body sensor, in which the body sensor includes a conductive electrode configured to conduct a biosignal from a body, a main board comprising a radio frequency (RF) communication circuit to generate an RF signal based on the biosignal, and an antenna disposed on the RF communication circuit to radiate the RF signal.

The body sensor may further include a ground layer disposed between the main board and the conductive electrode to reflect the RF signal radiated from the antenna to the body.

The body sensor may further include a gateway, in which the host device may be configured to control the body sensor using the gateway.

The gateway may be provided in a form of a portable electronic device.

In another general aspect, a method of transmitting a biosignal involves: detecting a biosignal of a user with a body sensor, the body sensor comprising a main board and an antenna disposed on the main board, using a radio frequency (RF) communication circuit inside the main board to generate an RF signal based on the biosignal, and transmitting the RF signal to a host device.

The detecting of the biosignal may involve disposing a conductive electrode of the body sensor over a body of the user.

A ground layer may be disposed between the main board and the conductive electrode, the method further involving transmitting the RF signal generated in the RF communication circuit through at least one electrical element that electrically connects the antenna to the main board through a via formed in the ground layer.

Other features and aspects will be apparent from the following detailed description, the drawings, and the claims.

BRIEF DESCRIPTION OF THE DRAWINGS

FIG. 15 illustrates another example of the antenna illustrated in FIG. 11.

Figure 1:
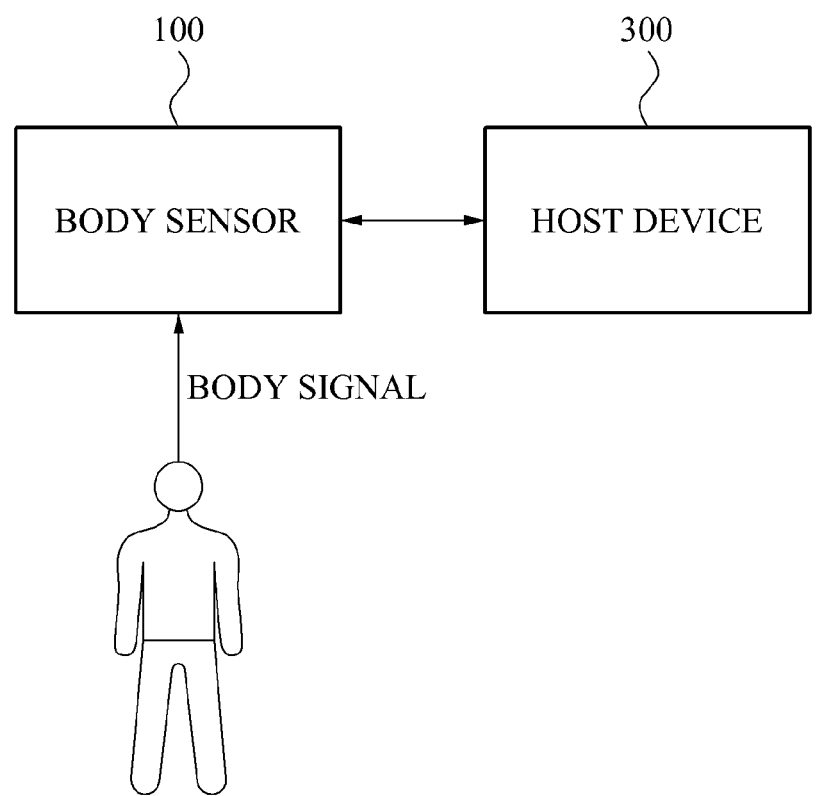
FIG. 1 is a block diagram illustrating an example of a system including a body sensor.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a block diagram illustrating an example of a system 10 including a body sensor 100. The system 10 may be a health monitoring system.

Referring to FIG. 1, the system 10 includes the body sensor 100 and a host device 300.

The body sensor 100 may be a patient monitor, an electrocardiogram (ECG) device, a respiratory rate sensor, a pulse rate sensor, a body temperature sensor, electric conduction sensor, a medical imaging device or the like.

The body sensor 100 may be wearable on a user, for example, a patient.

The body sensor 100 may monitor the user to which the body sensor 100 is attached.

In an example, the body sensor 100 may detect or measure a biosignal, may process the detected biosignal, and may transmit a radio frequency (RF) signal to the host device 300 as a result of the processing.

In this example, the term biosignal may refer to all types of signals that may be measured, monitored or detected, in a continual, intermittent or one time manner, from a biological being. For example, a biosignal may include a living body signal that may be obtained from a person who is alive and wearing the body sensor 100. In another example, the biosignal may be obtained from a person who is implanted with a body sensor 100.

The biosignal may include, but is not limited to, an electrocardiogram, an electromyogram, temperature, pulse rate, respiratory rate, vital signs, humidity, atmosphere, momentum, and/or other information known to those of ordinary skill in the art that may be obtained from biological beings.

In another example, the body sensor 100 may process the biosignal and may provide, based on a result of the processing, the appropriate therapy directly or indirectly to the user to whom the body sensor 100 is attached.

The body sensor 100 may transmit the RF signal based on the biosignal to the host device 300 through an antenna.

The host device 300 may be provided in a form of a portable electronic device. The portable electronic device may include a laptop computer, a mobile phone, a smart phone, a tablet personal computer (PC), a mobile internet device (MID), a personal digital assistant (PDA), an enterprise digital assistant (EDA), a digital still camera, a digital video camera, a portable multimedia player (PMP), a personal navigation device or a portable navigation device (PND), a handheld game console, and an e-book.

The host device 300 may control the body sensor 100. The host device 300 and the body sensor 100 may communicate with one another.

The host device 300 may continuously monitor, using the body sensor 100, a state of the user to whom the body sensor 100 is attached. As an example, the state of the user may refer to a health state, a physiological condition or a medical state of the user. For example, the host device 300 may receive the RF signal based on the biosignal output from the body sensor 100 and may display the state of the user corresponding to the biosignal on a display of the host device 300.

Also, the host device 300 may provide a service to the user attached with the body sensor 100 based on a result of the monitoring. For example, the host device 300 may provide therapy corresponding to the biosignal, directly or indirectly, to the user.

Figure 2:
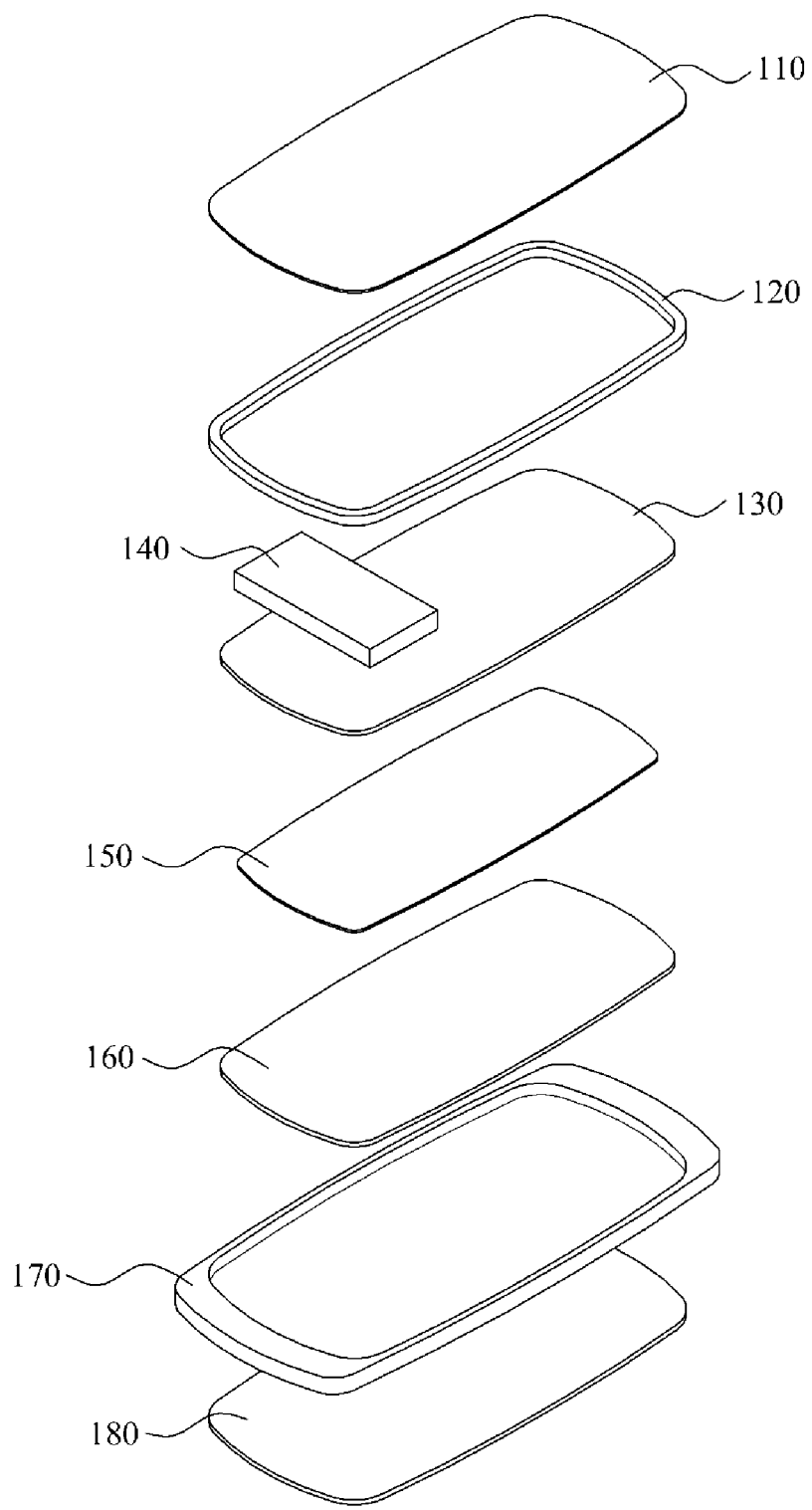
FIG. 2 is an exploded perspective view illustrating an example of a body sensor illustrated in FIG. 1.

FIG. 2 is an exploded perspective view illustrating an example of a body sensor 100 according to the example illustrated in FIG. 1

Referring to FIGS. 1 and 2, the body sensor 100 includes a top cover 110, a middle case 120, a main board 130, an antenna 140, a ground layer 150, an electrode interface 160, a bottom cover 170, and a conductive electrode 180.

The top cover 110 is disposed on the main board 130 and the antenna 140.

Components related to computation for the body sensor 100 may be attached to or mounted on, or inserted or embedded in the main board 130.

The components described in the foregoing may refer to various function blocks used for the body sensor 100. For example, the computing power house may include a central processing unit (CPU), a graphics processing unit (GPU), a memory, a universal serial bus (USB), a peripheral component interconnect (PCI), a digital signal processor (DSP), a wired interface, a wireless interface, a controller, an embedded software, a codec, a video module including a camera interface, a joint photographic experts group (JPEG) processor, a video processor, a mixer, an audio system, and a driver.

The antenna 140 may radiate or transmit an RF signal based on a biosignal to the host device 300.

The antenna 140 is disposed at an upper end of the main board 130. The antenna 140 may include an antenna carrier disposed on the main board 130 to support the antenna 140.

The middle case 120 may be formed in a physical supporting form for the body sensor 100. A height of the middle case 120 may be determined based on heights of the components of the body sensor 100 disposed on the main board 130. Also, when the antenna 140 includes the antenna carrier, the height of the middle case 120 may be determined based on a height of the antenna carrier.

The ground layer 150 is disposed between the main board 130 and the conductive electrode 180. For example, the ground layer 150 is disposed below the main board 130 and disposed on the electrode interface 160 and the conductive electrode 180.

The ground layer 150 may perform a shielding function. The ground layer 150 may reflect or shield the RF signal radiated from the antenna 140 to the body. For example, the ground layer 150 may totally reflect the RF signal based on a mirror effect.

The ground layer 150 may reflect the RF signal radiated from the antenna 140 to prevent the RF signal from being absorbed in the body of the user wearing the body sensor 100 and may improve radiation efficiency of the antenna 140.

In an example, the ground layer 150 may be provided in a form of a printed circuit board (PCB). For example, the ground layer 150 may be configured with a copper.

The electrode interface 160 may provide an interface for the main board 130 and the conductive electrode 180. In an example, the electrode interface 160 may be provided in a form of the PCB. For example, the electrode interface 160 may be composed of copper.

The bottom cover 170 may include the ground layer 150 and the electrode interface 160.

The conductive electrode 180 may receive the biosignal generated from the body. The conductive electrode 180 may transmit the received biosignal to the main board 130 through the electrode interface 160. The conductive electrode 180 may be disposed below the bottom cover 180. In an example, the conductive electrode 180 may be provided in a removable form.

The top cover 110, the middle case 120, and the bottom cover 170 may be provided in a form of external hardware covering the main board 130, the antenna 140, the ground layer 150, and the electrode interface 160 that are disposed in the body sensor 100. In an example, the top cover 110, the middle case 120, and the bottom cover 170 may be composed of metal, a synthetic resin or a combination thereof.

Figure 3:
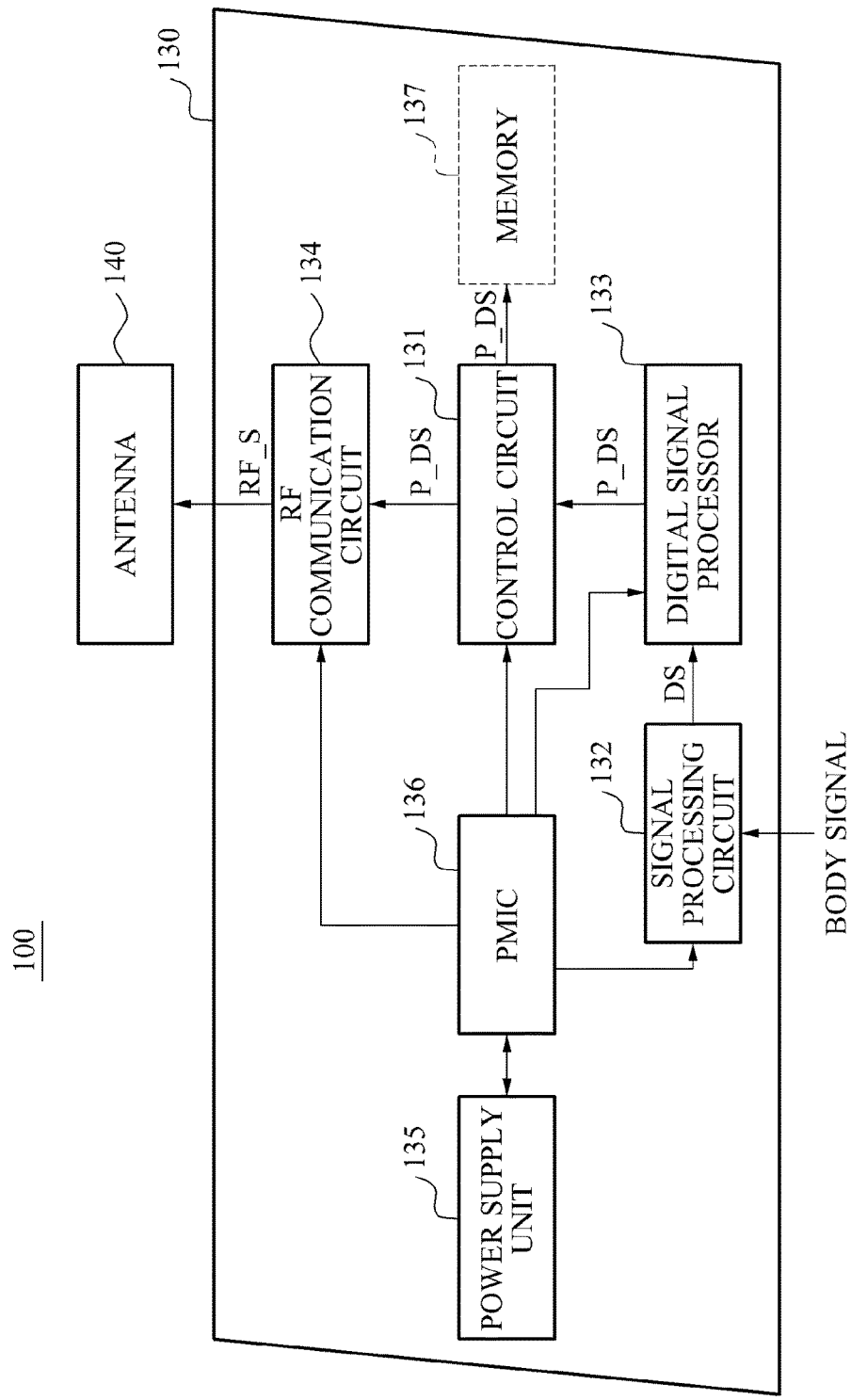
FIG. 3 is a block diagram illustrating an example of the body sensor illustrated in FIG. 1.

FIG. 3 is a block diagram illustrating an example of the body sensor 100 illustrated in FIG. 1.

Referring to FIGS. 1 through 3, the body sensor 100 may include a control circuit 131, a signal processing circuit 132, a digital signal processor 133, an RF communication circuit 134, a power supply unit 135, a power management integrated circuit (PMIC) 136, and an antenna 140. The body sensor 100 may further include a memory 137.

Individual components indicated as 131 through 137 may be attached to, mounted on, inserted, or embedded in a main board 130.

The main board 130 may be provided in a form of a PCB circuit such as a motherboard, an integrated circuit (IC), or a system on chip (SoC). The PCB may include a rigid PCB and a flexible PCB.

The control circuit 131 may control an overall operation of the body sensor 100. For example, the control circuit 131 may control the operation of each of the individual components indicated as 132 through 137.

In an example, the control circuit 131 may process a detected signal P_DS transmitted from the digital signal processor 133.

For example, the control circuit 131 may transmit the detected signal P_DS to the RF communication circuit 134 so that an RF signal RF_S, corresponding to the detected signal P_DS is transmitted to the host device 300 through the antenna 140.

In another example, the control circuit 131 may store the detected signal P_DS in the memory 137. The control circuit 131 may read the detected signal P_DS stored in the memory 137 and may transmit the signal to the RF communication circuit 134 so that the RF signal RF_S corresponding to the detected signal P_DS is transmitted to the host device 300 through the antenna 140. The detected signal may be a processed digital signal.

The signal processing circuit 132 may receive a biosignal through the electrode interface 160, may process the received biosignal, and may convert the biosignal to a digital signal DS.

For example, the signal processing circuit 132 eliminates noise from the biosignal. The signal processing circuit 132 may amplify the biosignal from which the noise is eliminated.

The signal processing circuit 132 may refer to an analog front-end (AFE). The signal processing circuit 132 may transmit the digital signal DS to the digital signal processor 133.

The digital signal processor 133 may receive and process the digital signal DS. The digital signal processor 133 may detect, based on the digital signal DS, a pathological event corresponding to the biosignal and may generate the detected signal P_DS as a result of the detecting. In an example, the detected signal P_DS may include the biosignal. The digital signal processor 133 may transmit the detected signal P_DS to the control circuit 131.

The RF communication circuit 134 may convert the detected signal P_DS to the RF signal RF_S and wirelessly transmit the RF signal RF_S to the antenna 140. The power supply unit 135 may supply power to the body sensor 100. In an example, the power supply unit 135 may supply the power to the main board 130. For example, the power supply unit 135 may be a battery. In another example, the power supply unit 135 may be wirelessly charged based on a wireless power transfer technology.

The PMIC 136 may control the power to be supplied by the power supply unit 135. For example, the PMIC 136 may control a power status of the body sensor 100. The power status may be indicated as a power-up status, a power-on status, a power-down status, or a power-off status. The power-up status may indicate a status in which power or voltage of the body sensor 100 is fully powered. The power-down status may indicate a status in which the power of the body sensor 100 is powered off, or the body sensor 100 enters a lower power mode.

The memory 137 may store the detected signal P_DS or may store data corresponding to the detected signal P_DS.

The memory 137 may be provided in a form of a volatile memory or nonvolatile memory.

The volatile memory may include a dynamic random access memory (DRAM), a static random access memory (SRAM), a thyristor RAM (T-RAM), a zero capacitor RAM (Z-RAM), and a Twin Transistor RAM (TTRAM).

The nonvolatile memory may include an electrically erasable programmable read-only memory (EEPROM), a flash memory, a magnetic RAM (MRAM), a spin-transfer torque (STT)-MRAM, a conductive bridging RAM (CBRAM), a ferroelectric RAM (FeRAM), a phase change RAM (PRAM), a resistive RAM (RRAM), a nanotube RRAM, a polymer RAM (PoRAM), a nano floating gate memory (NFGM), a holographic memory, a molecular electronic memory device, and an insulator resistance change memory.

The memory 137 may be disposed in the control circuit 131.

The antenna 140 may radiate or transmit the RF signal RF_S to the host device 300. The antenna 140 may radiate the RF signal RF_S based on Wireless Body Area Network (WBAN). For example, the antenna 140 may radiate the RF signal RF_S at a frequency of 2.4 GHz based on the WBAN. The WBAN may be a medical WBAN or a non-medical WBAN, but the network is not limited thereto.

Figure 4:
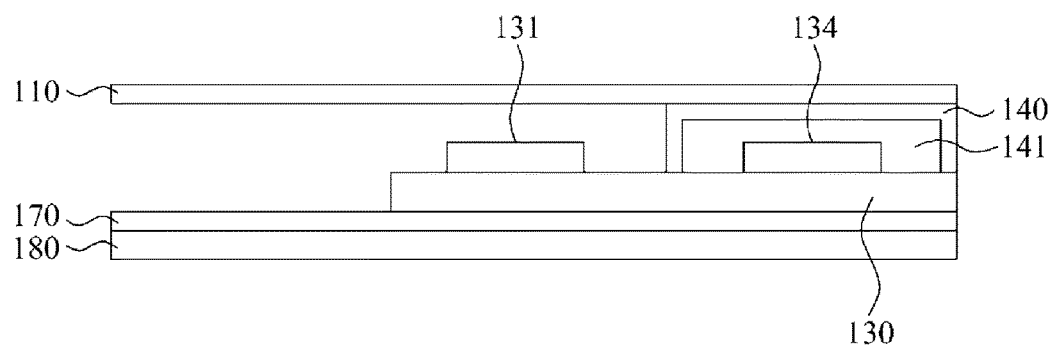
FIG. 4 is a cross-sectional view illustrating an example of a body sensor.

FIG. 4 illustrates a cross-sectional view of the body sensor 100 illustrated in FIG. 2. The body sensor 100 has a layered structure including a plurality of layers that are disposed on top of each other.

For convenience of description, FIG. 4 illustrates an example in which only the control circuit 131 and the RF communication circuit 134 are disposed on the main board 130.

Referring to FIGS. 1 through 4, the bottom cover 170 may be disposed on the conductive electrode 180. The bottom cover 170 may include the electrode interface 160 and the ground layer 150. The main board 130 may be disposed in the bottom cover 170, for example, disposed on the ground layer 150.

The antenna 140 may be disposed at an upper end of the main board 130. For example, the antenna 140 may be disposed on the RF communication circuit 134 to be in a vertical feeding structure.

A medium 141 disposed between the antenna 140 and the RF communication circuit 134 may indicate a space. For example, the space may be determined based on the antenna 140 and the RF communication circuit 134 disposed on the main board 130, but is not limited thereto, because the space may include all spaces defined as a bottom of the antenna 140 based on disposition of individual components indicated as 131 through 137 disposed on the main board 130. The space may be filled with air.

The medium 141 may be determined based on a dielectric constant, a dielectric loss factor or a combination thereof. For example, the medium 141 may be a material having a reasonable dielectric constant and a low dielectric loss factor.

For example, the material may include air, polyethylene, Teflon, polystyrene, nylon, pyrex glass, and the like.

Figure 5:
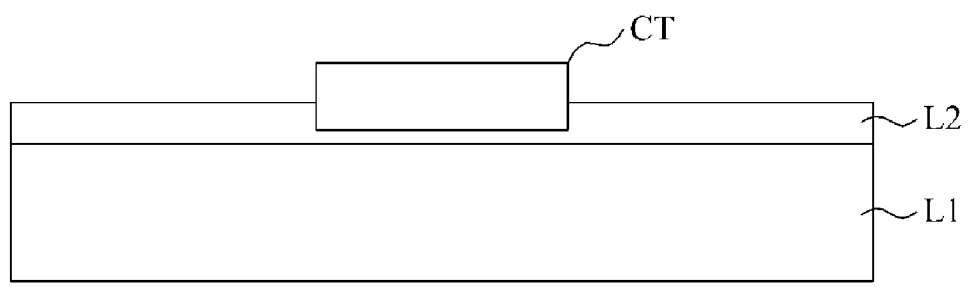
FIG. 5 is a cross-sectional view illustrating an example of a conductive electrode in the body sensor illustrated in FIG. 4.

FIG. 5 is a cross-sectional view illustrating an example of a conductive electrode 180 illustrated in FIG. 4. The conductive electrode 180 has a layered structure.

Referring to FIGS. 1 through 5, the conductive electrode 180 may include a first layer L1 and a second layer L2. In an example, the conductive electrode 180 may further include a conductive tape CT. The first layer L1 and the second layer L2 may be disposed as shown in FIG. 5.

The conductive electrode 180 may be in contact with a bottom cover 170 using the conductive tape CT. The conductive tape CT may increase a bonding strength between the conductive electrode 180 and the bottom cover 170 due to embossing effect. Also, the conductive tape CT may conduct or transmit a biosignal to the electrode interface 160 on the bottom cover 170.

Figure 6:
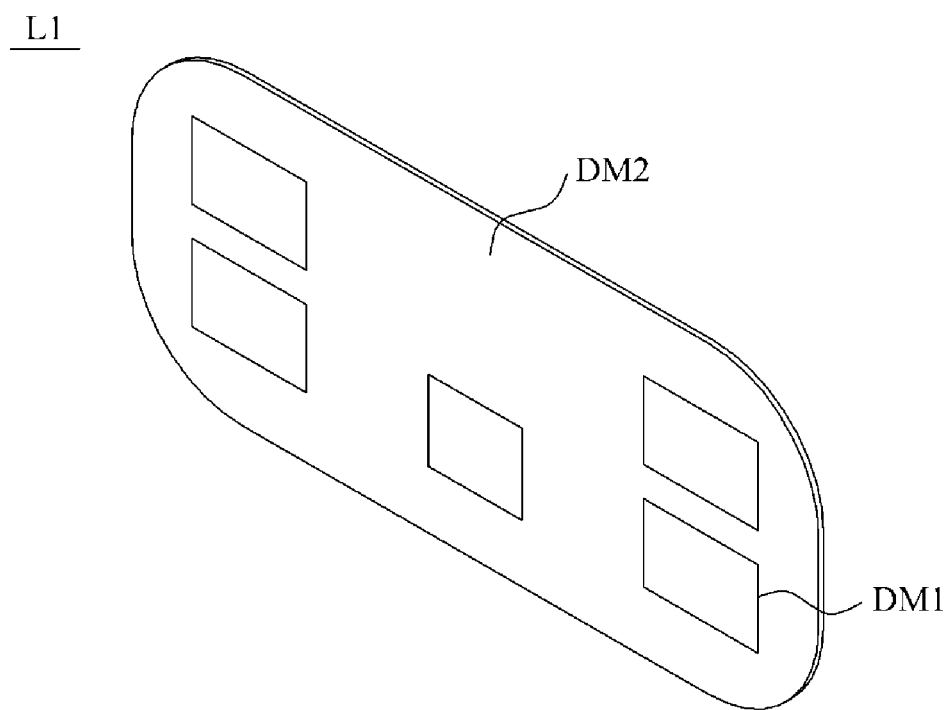
FIG. 6 is a perspective view illustrating an example of a first layer in the body senor illustrated in FIG. 4.

FIG. 6 is a perspective view illustrating an example of the first layer L1 illustrated in FIG. 4.

Referring to FIGS. 1 through 6, the first layer L1 may include one or more domains such as, for example, a first domain DM1 and a second domain DM2. A first domain DM1 may be filled with a hydrogel. For example, the hydrogel may conduct a biosignal, for example, an electrical signal generated from a body. A second domain DM2 may be provided in a polyethylene form.

Figure 7:
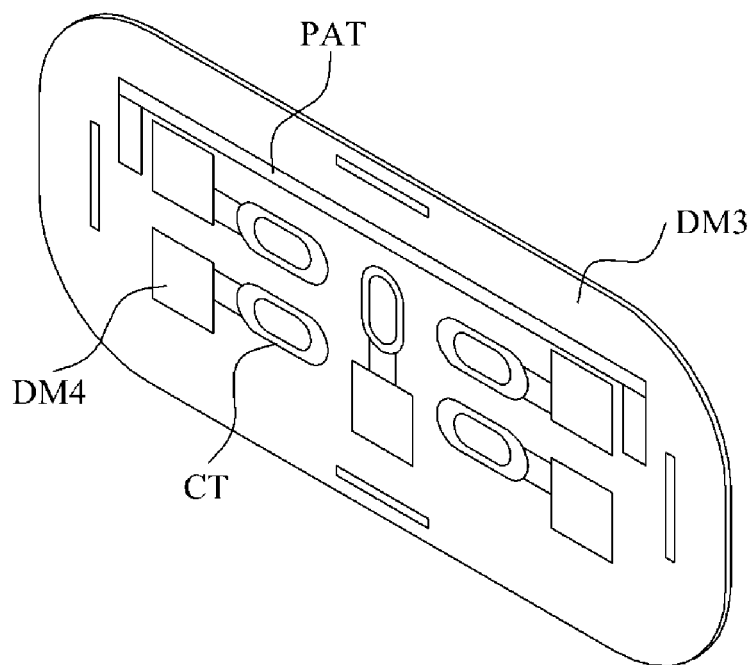
FIG. 7 is a perspective view illustrating an example of a second layer in the body sensor illustrated in FIG. 4.

FIG. 7 is a perspective view illustrating an example of the second layer L2 illustrated in FIG. 4.

Referring to FIGS. 1 through 7, the second layer L2 may include one or more domains such as, for example, a third domain DM3 and a forth domain DM4, and an electrode pattern PAT.

The electrode pattern PAT may be formed in the fourth domain DM 4 corresponding to a first domain DM1 of the first layer L1. In an example, the electrode pattern PAT may be formed with silver chloride (AgCl).

The conductive tape CT may be disposed in the middle of the second layer L2. The electrode pattern PAT formed in the forth domain DM4 may be connected to the conductive tape CT disposed in the middle of the second layer L2. Due to the electrode pattern PAT being connected to the conductive tape CT, electrodes of the conductive electrode 180 that are used to transmit a biosignal may be concentrated at a center of the second layer L2.

The third domain DM3 may be composed of a polyethylene terephthalate film.

Figure 8:
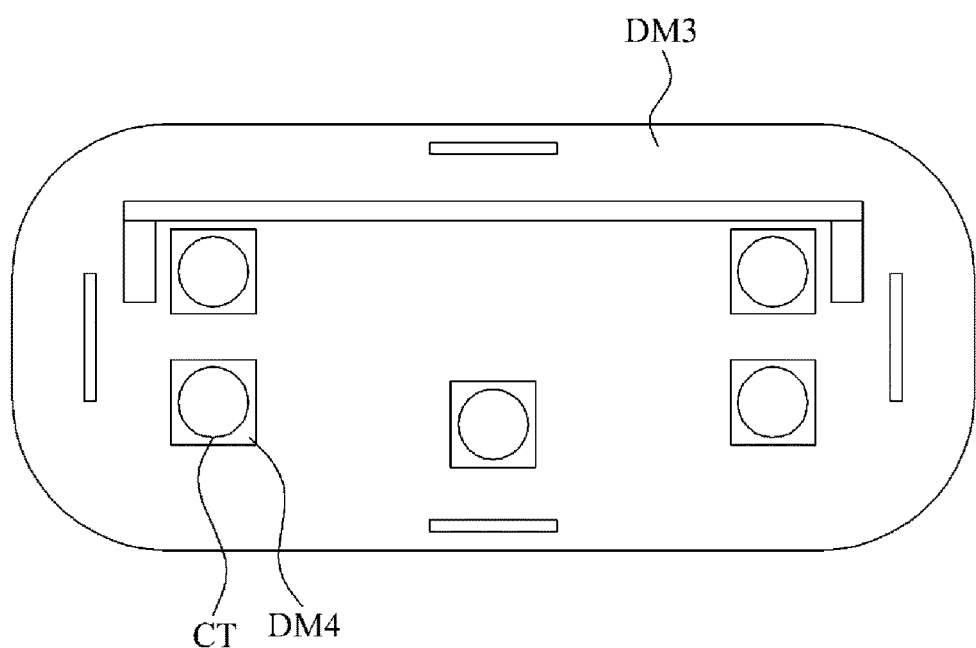
FIG. 8 is a plan view illustrating an example of the second layer illustrated in FIG. 4.

FIG. 8 illustrates a plan view of an example of the second layer L2 according to the example illustrated in FIG. 4.

Referring to FIGS. 1 through 6 and 8, the second layer L2 may include one or more domains such as, for example, a third domain DM3 and a forth domain DM4, and a electrode pattern PAT.

The electrode pattern PAT may formed in fourth domain DM4 corresponding to first domain DM1 of the first layer L1. In an example, the electrode pattern PAT may be formed with silver chloride (AgCl).

The conductive tape CT may be disposed on the electrode pattern PAT formed in the fourth domain DM4. Due to the conductive tape CT being disposed on the electrode pattern PAT formed in the fourth domain DM4, a form in which electrodes of the conductive electrode 180 used to transmit a biosignal are dispersed may be formed.

The third domain DM3 may be composed of a polyethylene terephthalate film.

Figure 9A:
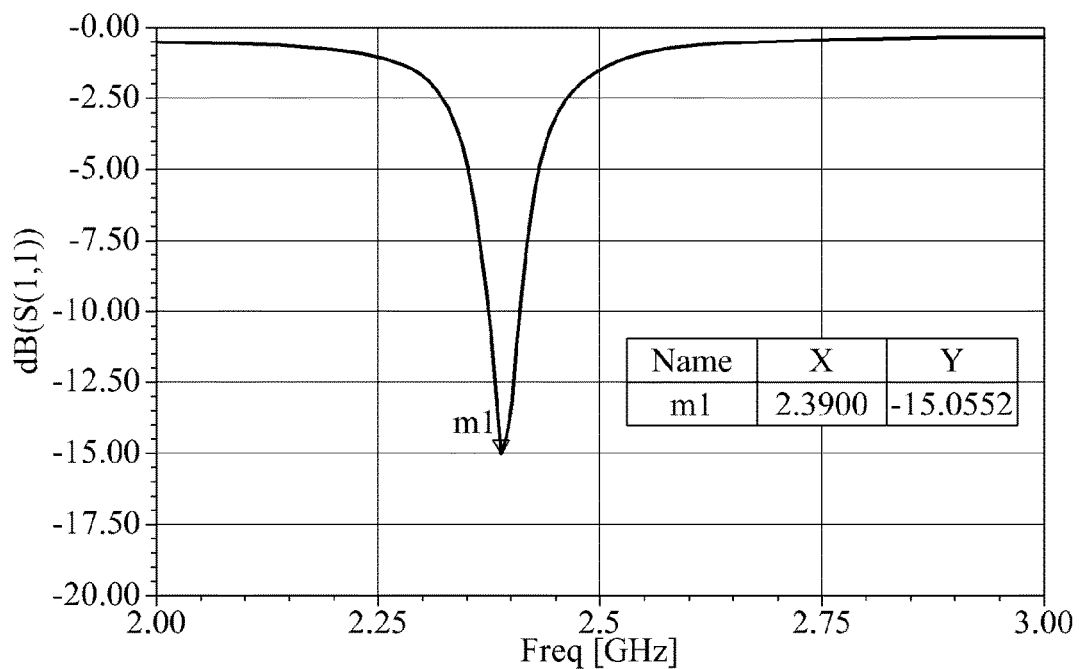
FIGS. 9A and 9B are graphs illustrating examples of a relationship between a conductive electrode and a ground layer in a body senor in which a second layer of the conductive electrode illustrated in FIG. 4 is configured in a same manner as the second layer illustrated in FIG. 7 or FIG. 8.
Figure 9B:
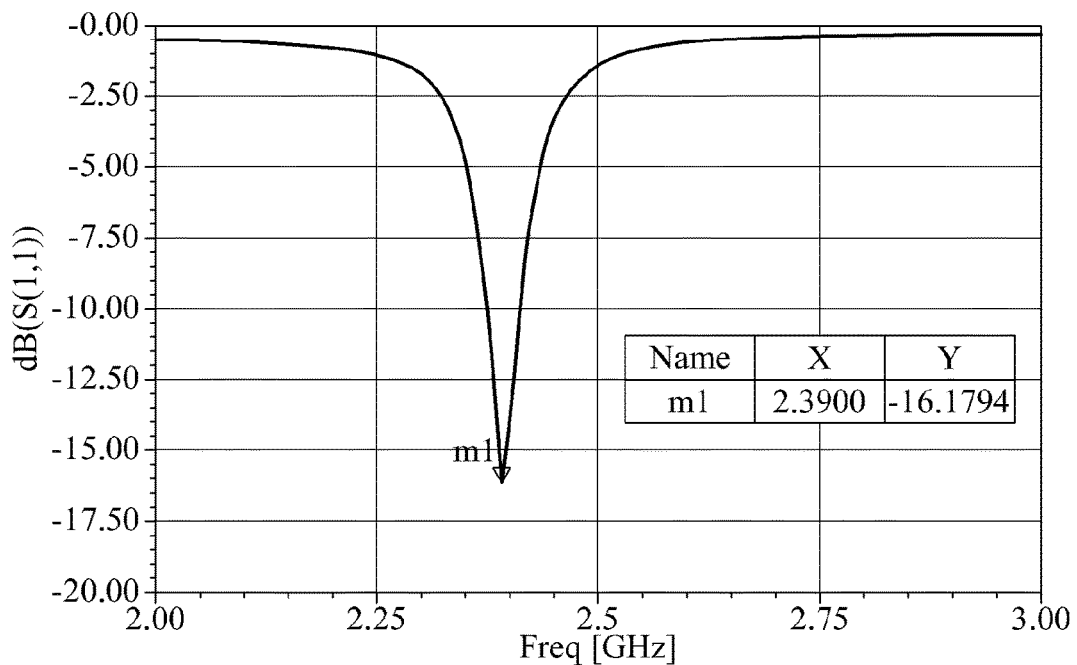

FIGS. 9A and 9B are graphs illustrating an example of a relationship between a conductive electrode 180 and a ground layer 150 when a second layer of the conductive electrode 180 illustrated in FIG. 4 is configured in a same manner as the second layer L2, illustrated in FIG. 7 and FIG. 8.

Referring to FIGS. 1 through 9B, as shown in FIGS. 7 and 8, electrodes of the conductive electrode 180 may be concentrated or dispersed.

In the graphs illustrated in FIGS. 9A and 9B, a frequency may be indicated on an x axis and a reflection coefficient on a y axis.

When the second layer of the conductive electrode 180 is configured in the same manner as the second layer L2 of FIG. 7 in which the electrodes are concentrated, the relationship between the conductive electrode 180 and the ground layer 150 may be as shown in the graph illustrated in FIG. 9A.

When the second layer of the conductive electrode 180 is configured in the same manner as the second layer L2 of FIG. 8 in which the electrodes are dispersed, the relationship between the conductive electrode 180 and the ground layer 150 may be as shown in the graph illustrated in FIG. 9B.

As shown in the graphs illustrated in FIGS. 9A and 9B, the reflection coefficient of the ground layer 150 may be essentially identical, irrespective of an electrode form of the conductive electrode 180. For example, in a 2.4 GHz frequency band, the reflection coefficient of the ground layer 150 may be essentially identical.

Figure 10:
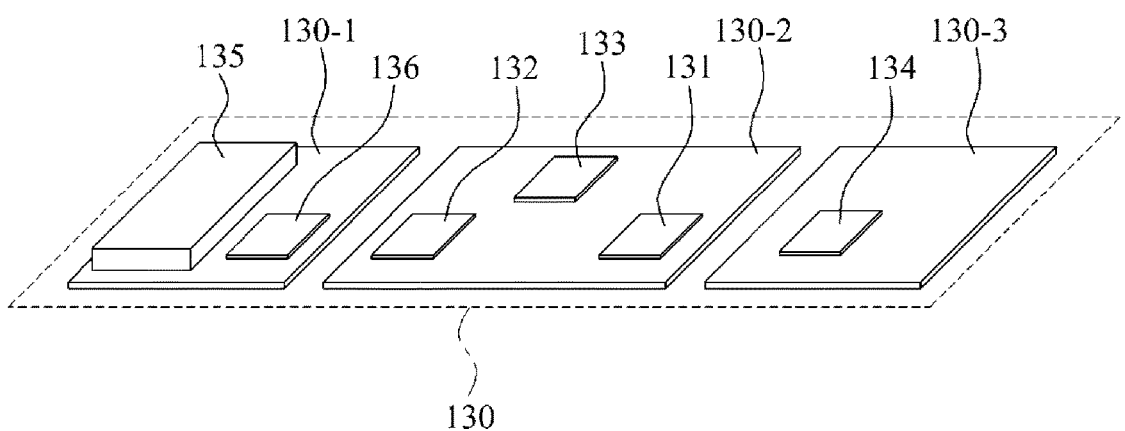
FIG. 10 is a perspective view illustrating an example of the main board illustrated in FIG. 4.

FIG. 10 is a perspective view illustrating an example of the main board 130 illustrated in FIG. 4.

Referring to FIGS. 1 through 10, the main board 130 may be configured in a form of at least one segmented structure. For example, the main board 130 may include a first main board 130-1, a second main board 130-2, and a third main board 130-3.

Individual main boards illustrated as 130-1 through 130-3 may be provided in a form of a PCB circuit such as a motherboard, an IC, or a SoC. In an example, the PCB may include a rigid PCB and a flexible PCB (FPCB).

The power supply unit 135 and the PMIC 136 may be attached to or mounted on, or inserted or embedded in the first main board 130-1. The control circuit 131, the signal processing circuit 132, and the digital signal processor 133 may be attached to, mounted on, inserted or embedded in the second main board 130-2. The RF communication circuit 134 may be attached to, mounted on, inserted or embedded in the third main board 130-3.

The antenna 140 may be disposed on the third main board 130-3. For example, the antenna 140 may be disposed on the RF communication circuit 134.

Figure 11:
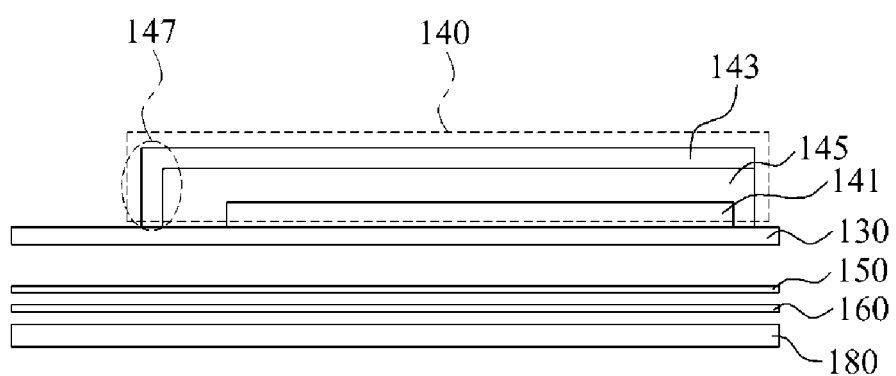
FIG. 11 is a cross-sectional view illustrating another example of the body sensor illustrated in FIG. 2.

FIG. 11 is a cross-sectional view illustrating another example of the body sensor 100 illustrated in FIG. 2.

Referring to FIGS. 1 through 11, the electrode interface 160 may be disposed on the conductive electrode 180.

The electrode interface 160 and the main board 130 may be electrically connected through at least one electrical element. The electrode interface 160 may transmit a biosignal transmitted or conducted from the conductive electrode 180 through the at least one electrical element to the signal processing circuit 132 of the main board 130. For example, the at least one electrical element may be provided in a form of a through-hole via.

The ground layer 150 may be disposed on the electrode interface 160. The main board 130 may be disposed on the ground layer 150. For example, the ground layer 150 may be disposed between the conductive electrode 180 and the main board 130.

The main board 130 and the ground layer 150 may be electrically connected through at least one electrical element. The main board 130 may be connected to the ground layer 150 through the at least one electrical element. For example, the at least one electrical element may be provided in a form of the through-hole via.

The antenna 140 may be disposed at an upper end of the main board 130. For example, the antenna 140 may be disposed on an RF communication circuit 134 to be in a vertical feeding structure.

The antenna 140 may include an antenna layer 143, an antenna carrier 145, and an antenna feeder 147.

The antenna layer 143 may include an antenna pattern to radiate or transmit an RF signal, for example, RF signal RF_S. For example, the antenna pattern may include a ground pattern to be connected to a signal pattern to radiate the RF signal RF_S.

The antenna carrier 145 may support the antenna layer 143. The antenna layer 143 may be disposed on top of the body sensor 100 through the antenna carrier 143 and thus, the antenna layer 143 may be disposed farthest from a body.

Accordingly, the body sensor 100 may prevent the RF signal RF_S transmitted from the antenna layer 143 from being absorbed in the body and increase radiation efficiency or transmission efficiency of the antenna 140.

The antenna 140 may receive the RF signal RF_S transmitted from the RF communication circuit 134 through the antenna feeder 147 of the antenna pattern.

The antenna 140 may be disposed on the RF communication circuit 134 to be in the vertical feeding structure and thus, the body sensor 100 may prevent a loss of the RF signal RF_S transmitted from the RF communication circuit 134.

The antenna 140 and the ground layer 150 may be electrically connected through at least one electrical element. The antenna 140 may be connected to the ground layer 150 through the at least one electrical element. For example, the antenna 140 may be connected to the ground layer 150 through the antenna feeder 147 of the antenna pattern and the at least one electrical element. For example, the main board 130 and the ground layer 150 may be electrically connected through the at least one electrical element, and the antenna 140 may be connected to the main board 130 through the antenna feeder 147. Thus, the antenna 140 may be connected to the ground layer 150. For example, the at least one electrical element may be provided in a form of the through-hole via.

In an example, the antenna feeder 147 may be connected to the main board 130 through a coaxial jack, a C clip, or a pogo pin or a spring pin.

Figure 12:
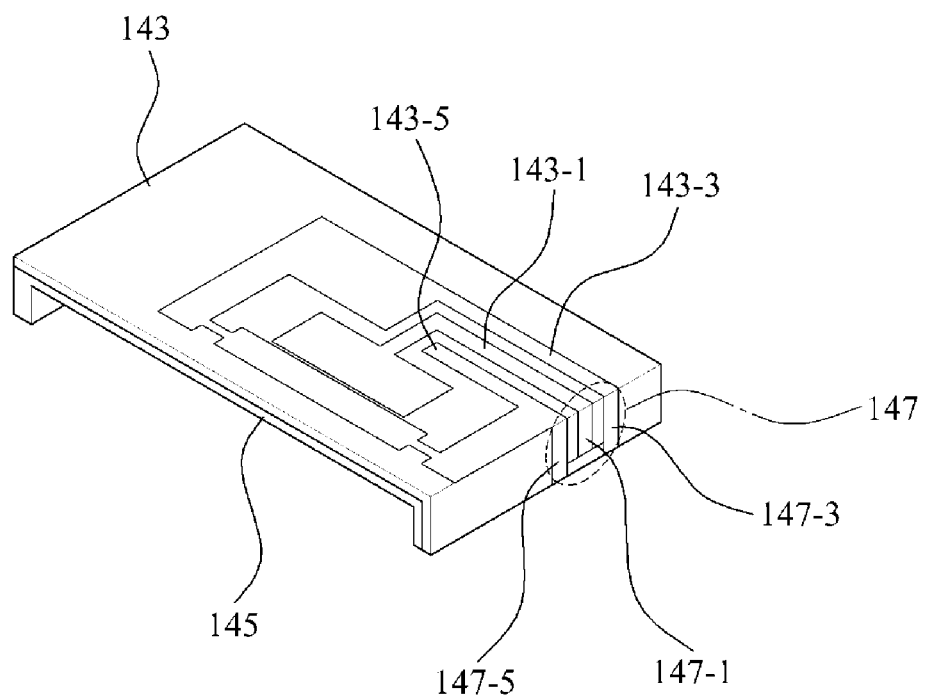
FIG. 12 is a perspective view illustrating an example of the antenna illustrated in FIG. 11.

FIG. 12 is a perspective view illustrating an example of the antenna 140 illustrated in FIG. 11.

Referring to FIGS. 1 through 12, an antenna 140-1 illustrated in FIG. 12 is an example of the antenna 140 illustrated in FIG. 11.

The antenna 140-1 may include the antenna layer 143 and the antenna carrier 145.

The antenna layer 143 may include an antenna pattern, for example, 143-1, 143-3, and 143-5, and an antenna feeder 147.

The antenna pattern may radiate or transmit an RF signal RF_S. For example, the antenna pattern may radiate the RF signal RF_S in a horizontal direction. For example, the antenna 140-1 may be a Zeroth Order Resonator (ZOR) antenna.

The antenna pattern may include a signal pattern 143-1 and ground patterns 143-3 and 143-5. In an example, the antenna pattern may be composed of gold, silver, or copper.

The signal pattern 143-1 may be a pattern used to radiate the RF signal RF_S. Both patterns, for example, 143-3 and 143-5, may be the ground patterns to be connected to the ground layer 150.

The antenna feeder 147 may include a signal feeder 147-1 and ground feeders, for example, 147-3 and 147-5. The signal pattern 143-1 may receive the RF signal RF_S transmitted from the RF communication circuit 134 through the signal feeder 147-1, and may radiate the received RF signal RF_S. The ground patterns 143-3 and 143-5 may be electrically connected to the ground layer 150 through the corresponding ground feeders 147-3 and 147-5. For example, one ground pattern 143-3 of the ground patterns 143-3 and 143-5 may be connected to the ground layer 150 through one ground feeder 147-3 of the ground feeders 147-3 and 147-5 and the other ground pattern 143-5 of the ground patterns 143-3 and 143-5 may be connected to the ground layer 150 through the corresponding ground feeder 147-5 of the ground feeders 147-3 and 147-5.

Figure 13A:
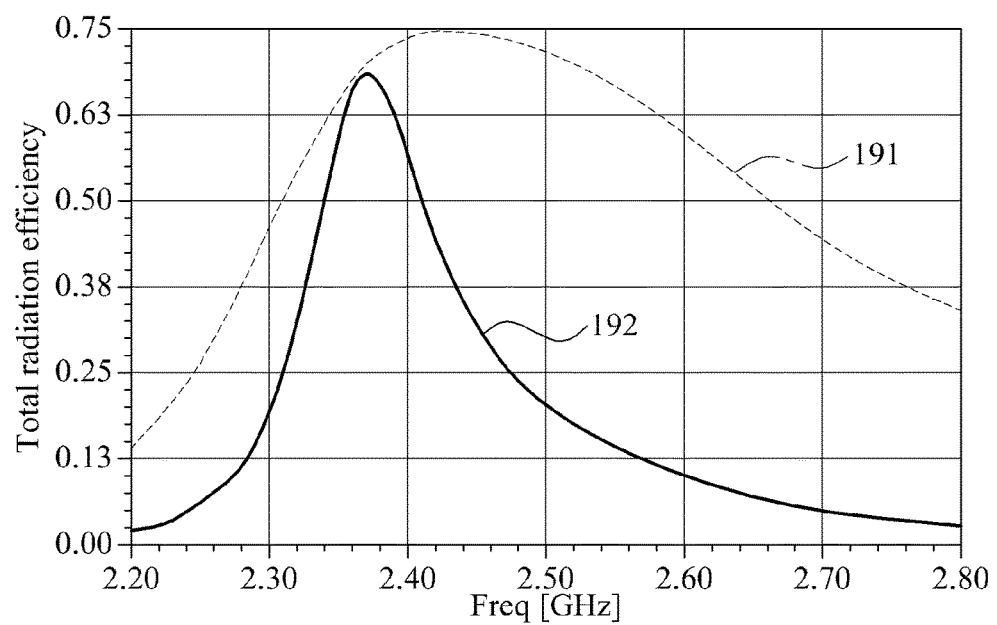
FIGS. 13A and 13B are graphs illustrating examples of radiation efficiency of the antenna illustrated in FIG. 12.
Figure 13B:
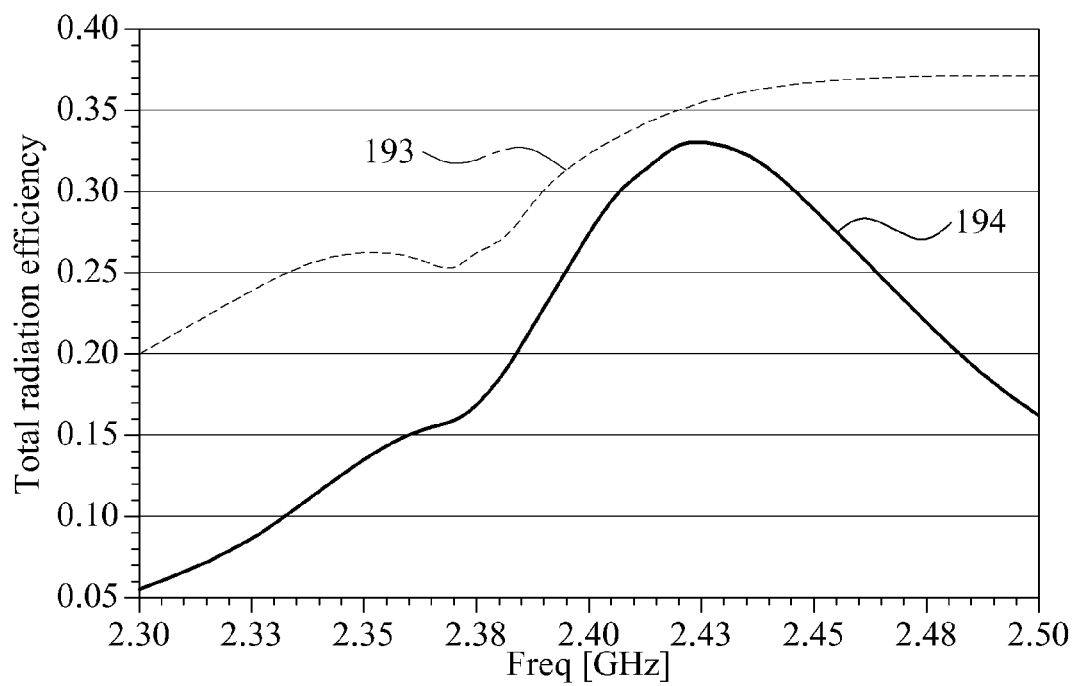

FIGS. 13A and 13B are graphs illustrating an example of radiation efficiency of the antenna 140-1 illustrated in FIG. 12.

Referring to FIGS. 1 through 13B, the antenna 140-1 may radiate or transmit an RF signal RF_S, in a horizontal direction.

In the graphs illustrated in FIGS. 13A and 13B, a frequency is indicated on an x axis, and a total radiation efficiency of the antenna 140-1 is indicated on a y axis.

The graph of FIG. 13A indicates a total radiation efficiency of the antenna 140-1 when the body sensor 100 is not worn on a body. That is, FIG. 13A indicates the total radiation efficiency of the antenna 140-1 taken while the body sensor 100 is in a free-space. A dotted line 191 does not reflect a structure of the antenna feeder 147 of the antenna 140-1, and a solid line reflects the result of implementing the structure of the antenna feeder 147 of the antenna 140-1. When the body sensor 100 is not worn on the body, the radio efficiency of the antenna 140-1 in a 2.4 GHz frequency band may correspond to the graph illustrated in FIG. 13A.

The graph of FIG. 13B indicates a total radiation efficiency of the antenna 140-1 when the body sensor 100 is worn on the body. That is, FIG. 13B indicates the total radiation efficiency of the antenna 140-1 taken while the body sensor 100 is on the body. A dotted line 193 does not reflect the structure of the antenna feeder 147 of the antenna 140-1, and a solid line reflects the result of implementing the structure of the antenna feeder 147 of the antenna 140-1. When the body sensor 100 is worn on the body, the radio efficiency of the antenna 140-1 in a 2.4 GHz frequency band may be as illustrated in FIG. 13B.

Figure 14:
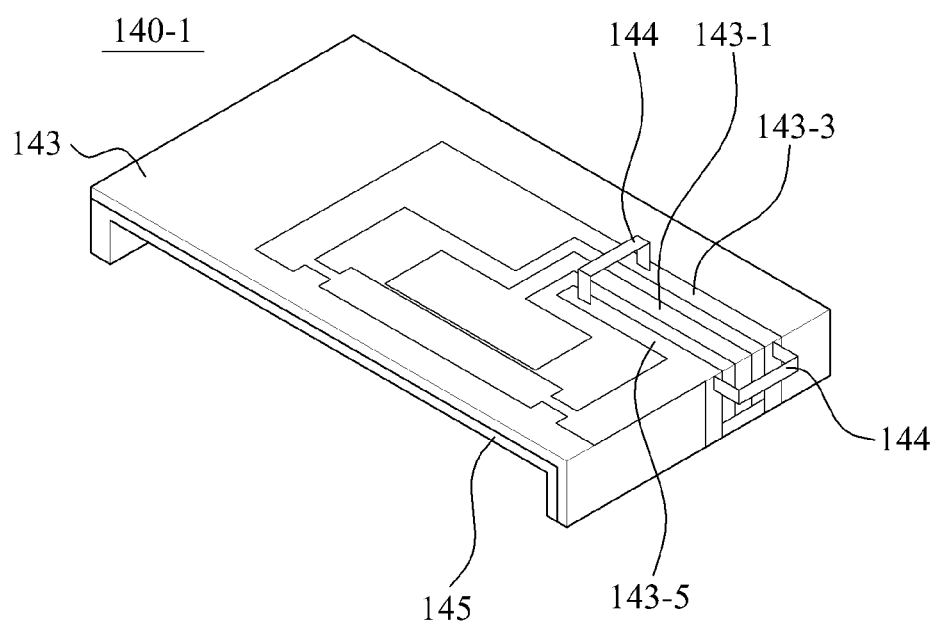
FIG. 14 is a perspective view illustrating an example of the antenna illustrated in FIG. 12.

FIG. 14 is a perspective view illustrating an example of the antenna 140-1 illustrated in FIG. 12.

Referring to FIGS. 1 through 14, the antenna 140-1 may further include an air bridge 144.

The air bridge 144 may be electrically connected to the ground patterns 143-3 and 143-5. Due to the ground patterns 143-3 and 143-5 being connected to each other through the air bridge 144, the antenna 140-1 may prevent resonance caused when an operating frequency or a resonant frequency of an RF signal RF_S is similar to a length of the main board 130. Also, the antenna 140-1 may not operate in an odd mode.

Thus, the antenna 140-1 may prevent the resonance and the odd mode using the air bridge 144, and may increase radiation efficiency of the antenna 140-1.

FIG. 15 illustrates another example of the antenna 140 illustrated in FIG. 11.

Referring to FIGS. 1 through 11 and 15, an antenna 140-2 illustrated in FIG. 15 is another example of the antenna 140 illustrated in FIG. 11.

The antenna 140-2 may be an antenna based on a metamaterial structure. For example, the antenna 140-2 may be an artificial magnetic conductor (AMC) antenna.

The antenna 140-2 may include the antenna layer 143 and the antenna carrier 145. For convenience of description, the antenna carrier 145 is not illustrated in FIG. 15.

The antenna layer 143 may include, for example, an antenna pattern PAT2. The antenna pattern PAT2 may include a signal pattern and a ground pattern. For example, the antenna pattern PAT2 may be a planar inverted F antenna (PIFA) or a patch antenna.

The antenna layer 143 may further include a ground plane 149. The ground plane 149 may include a ground pattern PAT3. In an example, the ground pattern PAT3 may be formed with at least one artificial magnetic conductor unit cell. The antenna pattern PAT2 and the ground pattern PAT3 may be composed of gold, silver, or copper.

The antenna 140-2 may block an influence of the RF communication circuit 134 disposed below the antenna 140-2 through the ground plane 149 and thus, increase radiation efficiency.

Figure 16:
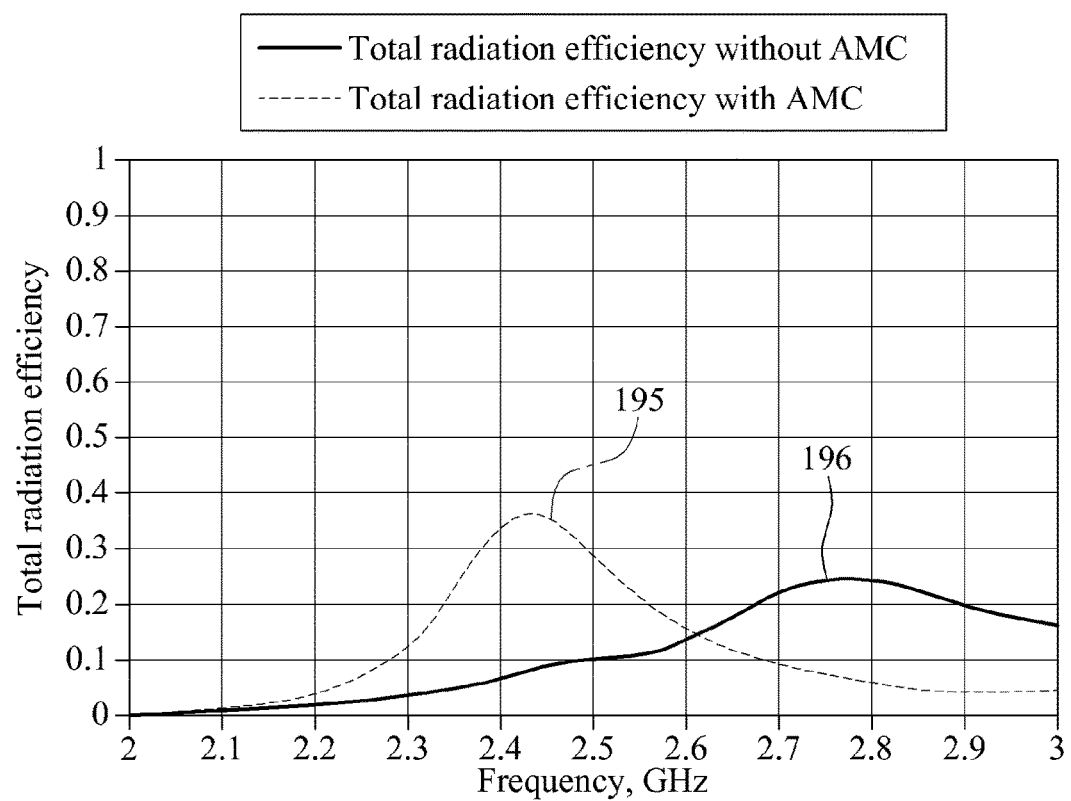
FIG. 16 is a graph illustrating an example of radiation efficiency of the antenna illustrated in FIG. 15.

FIG. 16 is a graph illustrating an example of radiation efficiency of an antenna illustrated in FIG. 15.

FIG. 16 is a graph illustrating an example of radiation efficiency of the antenna 140-2 illustrated in FIG. 15.

Referring to FIGS. 1 through 11, and 15 and 16, a frequency is indicated on an x axis and a total radiation efficiency of the antenna 140-2 is indicated on a y axis of the graph illustrated in FIG. 15.

The graph of FIG. 15 indicates a total radiation efficiency of the antenna 140-2 while the body sensor 100 is worn on a body. In the event that the ground plane 149 of the antenna 140-2 exists, the radiation efficiency of the antenna 140-2 in a 2.4 GHz frequency band may be shown as a third dotted line 195. The ground plane 149 may be formed with at least one artificial magnetic conductor unit cell. In the event that the ground plane 149 of the antenna 140-2 does not exist, the radiation efficiency of the antenna 140-2 in a 2.4 GHz frequency band may be shown as a third dotted line 196.

Figure 17:
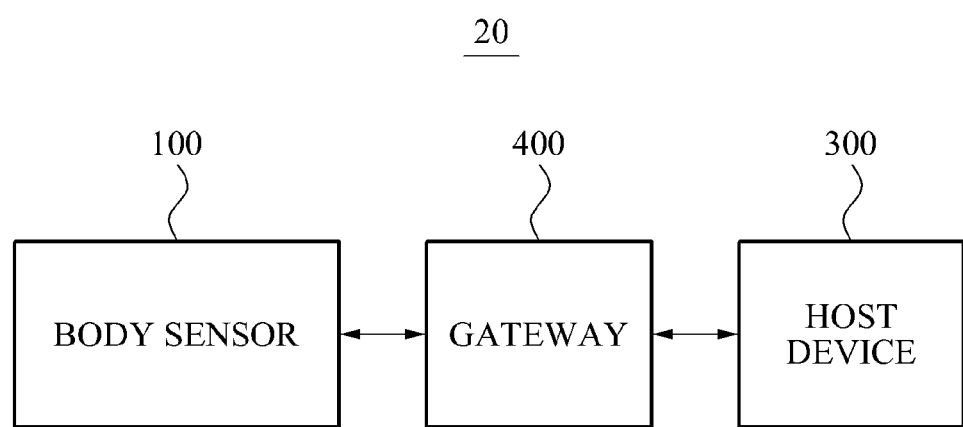
FIG. 17 is a diagram illustrating another example of a system including a body sensor.

FIG. 17 is a diagram illustrating another example of a system 20 including the body sensor 100. The system 20 may be a health monitoring system.

Referring to FIG. 17, the system 20 may include the body sensor 100, a gateway 400, and the host device 300.

The body sensor 100 and the host device 300 may communicate through the gateway 400.

The gateway 400 may be provided in a form of a portable electronic device. The portable electronic device may include a laptop computer, a mobile phone, a smart phone, a tablet PC, an MID, a PDA, an EDA, a digital still camera, a digital video camera, a PMP, a personal navigation device or a PND, a handheld game console, and an e-book.

The host device 300 may be a medical system used by a medical institution.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy discs, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

As a non-exhaustive illustration only, a terminal or device described herein may refer to mobile devices such as a cellular phone, a PDA, a digital camera, a portable game console, and an MP3 player, a portable/personal multimedia player (PMP), a handheld e-book, a portable laptop PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A wearable body sensor comprising:
   a conductive electrode configured to conduct a biosignal from a body;
   a main board comprising a radio frequency (RF) communication circuit to generate an RF signal based on the biosignal; and
   an antenna disposed on the RF communication circuit to radiate the RF signal, the antenna comprising a signal pattern configured to transmit the RF signal and disposed parallel to and between ground patterns electrically connected to a ground layer, the signal pattern comprising a first section and a second section perpendicular to the first section,
   wherein the antenna further comprises air bridges disposed orthogonally relative to each other and configured to electrically connect the ground patterns, the signal pattern and a signal feeder disposed orthogonally to the signal pattern being underneath the air bridges.

2. The body sensor of claim 1, further comprising:
   a ground layer disposed between the main board and the conductive electrode to reflect the RE signal radiated from the antenna to the body.

3. The body sensor of claim 2, further comprising:
   at least one electrical element configured to electrically connect the main board and the ground layer.

4. The body sensor of claim 2, further comprising:
   at least one electrical element configured to electrically connect the antenna and the ground layer.

5. The body sensor of claim 4, wherein the at least one electrical element is provided in a form of a through-hole via.

6. The body sensor of claim 1, further comprising:
   an electrode interface configured to transmit the biosignal to the main board.

7. The body sensor of claim 6, further comprising:
   at least one electrical element configured to electrically connect the electrode interface and the main board.

8. The body sensor of claim 7, wherein the at least one electrical element is provided in a form of a through-hole via.

9. The body sensor of claim 1, wherein the main board is configured in a form of at least one segmented structure.

10. The body sensor of claim 1, wherein the antenna comprises an antenna pattern configured to radiate the RF signal and an antenna layer disposed at an upper end of the RF communication circuit to be in a vertical feeding structure.

11. The body sensor of claim 10, wherein the antenna further comprises an antenna carrier configured to support the antenna layer.

12. The body sensor of claim 10, wherein the antenna pattern is configured to radiate the RF signal in a horizontal direction.

13. The body sensor of claim 1, further comprising a C-shaped air bridge connecting the ground patterns to prevent resonance and a second air bridge connecting the ground layer.

14. The body sensor of claim 10, wherein the antenna layer further comprises a ground plane connected to the antenna pattern.

15. The body sensor of claim 14, wherein the ground plane comprises at least one artificial magnetic conductor unit cell.

16. The body sensor of claim 10, wherein an antenna feeder of the antenna pattern is connected to the main board through a coaxial jack, a C clip, or a pogo pin.

17. The body sensor of claim 1, wherein the body sensor is configured to measure at least one of electrocardiogram, electromyogram, body temperature, heart rate, electric conduction, and blood pressure of the body wearing the body sensor.

18. The body sensor of claim 1, wherein the first section of the signal pattern is disposed directly adjacent to a first section of one of the ground patterns, and the second section of the signal pattern is disposed directly adjacent to a second section of the one of the ground patterns.

19. A system, comprising:
a body sensor wearable on a body; and
a host device configured to control the body sensor, wherein the body sensor comprises:
a conductive electrode configured to conduct a biosignal from a body;
a main board comprising a radio frequency (RF) communication circuit to generate an RF signal based on the biosignal; and
an antenna disposed on the RF communication circuit to radiate the RF signal, the antenna comprising a signal pattern configured to transmit the RF signal and disposed parallel to and between ground patterns electrically connected to a ground layer, the signal pattern comprising a first section and a second section perpendicular to the first section,
wherein the antenna further comprises air bridges disposed orthogonally relative to each other and configured to electrically connect the ground patterns, the signal pattern and a signal leeder disposed orthogonally to the signal pattern being underneath the air bridges.

20. The system of claim 19, further comprising a gateway, wherein the host device is configured to control the body sensor using the gateway.

21. The system of claim 20, wherein the gateway is provided in a form of a portable electronic device.

22. The system of claim 19, wherein the body sensor further comprises a ground layer disposed between the main board and the conductive electrode to reflect the RF signal radiated from the antenna to the body.

23. A method of transmitting a biosignal, the method comprising:
detecting a biosignal of a user with a body sensor, the body sensor comprising a main board and an antenna disposed on the main board;
using a radio frequency (RF) communication circuit inside the main board to generate an RF signal based on the biosignal; and
transmitting the RE signal to a host device using a signal pattern disposed on the antenna, the signal pattern disposed parallel to and between ground patterns electrically connected to a ground layer, the signal pattern comprising a first section and a second section perpendicular to the first section,
wherein the antenna further comprises air bridges disposed orthogonally relative to each other and configured to electrically connect the ground patterns, the signal pattern and a signal leeder disposed orthogonally to the signal pattern being underneath the air bridges.

24. The method of claim 23, wherein a ground layer is disposed between the main board and the conductive electrode, the method further comprising transmitting the RE signal generated in the RF communication circuit through at least one electrical element that electrically connects the antenna to the main board through a via formed in the ground layer.

25. The method of claim 23, wherein the detecting of the biosignal comprises disposing a conductive electrode of the body sensor over a body of the user.

* * * * *

UNITED STATES PATENT AND TRADEMARK OFFICE
CERTIFICATE OF CORRECTION

PATENT NO. : 10,084,230 B2
APPLICATION NO. : 14/508602
DATED : September 25, 2018
INVENTOR(S) : Hong et al.

Page 1 of 1

It is certified that error appears in the above-identified patent and that said Letters Patent is hereby corrected as shown below:

On the Title Page

Page 2, Column 2, in item (56) "References Cited," under "OTHER PUBLICATIONS," Line 17, insert --Chinese Office Action issued on May 25, 2018, in counterpart Chinese Application No. 201410293678.3 (9 pages, in Korean, no English translation).-- as the last document in the list.

Signed and Sealed this
Twenty-first Day of May, 2019

Andrei Iancu
*Director of the United States Patent and Trademark Office*